United States Patent [19]

Cieslak et al.

[11] 4,281,418
[45] Aug. 4, 1981

[54] PORTABLE FURNACE FOR WEARING APPAREL

[76] Inventors: Stanley Cieslak, 14 Creek Rd.; Leonard K. Cieslak, 15 Creek Rd., both of McKees Rocks, Pa. 15136

[21] Appl. No.: 49,059

[22] Filed: Jun. 18, 1979

Related U.S. Application Data

[63] Continuation-in-part of Ser. No. 875,815, Feb. 7, 1978.

[51] Int. Cl.³ .................. A41D 19/00; A43B 7/02; A41F 7/00
[52] U.S. Cl. .................................... 2/160; 36/2.6; 126/206
[58] Field of Search ............... 36/2.6; 2/160, 161 A; 126/204, 206, 207

[56] References Cited

U.S. PATENT DOCUMENTS

| | | | |
|---|---|---|---|
| 912,527 | 2/1909 | Batter | 36/2.6 |
| 3,000,616 | 9/1961 | Spangler | 36/2.6 |
| 3,712,288 | 1/1973 | Weiss | 126/206 |
| 4,094,080 | 6/1978 | Sanders | 36/2.6 |
| 4,118,946 | 10/1978 | Tubin | 126/204 |

Primary Examiner—Patrick D. Lawson
Attorney, Agent, or Firm—Carothers and Carothers

[57] ABSTRACT

A portable furnace for generating and circulating heat in wearing apparel. The furnace consists of a compact insulated case having a cavity therein which is adapted to receive slow burning solid fuel agglomerates for combustion. A liquid reservoir is positioned in the case for radiant heat transfer from the ignited fuel agglomerates in the cavity. A flexible liquid conduit has opposite ends thereof connected for circulation of the heated liquid from the reservoir in a closed circuit, and a pump is provided for hand manipulation to circulate the heated liquid through the conduit on demand.

10 Claims, 9 Drawing Figures

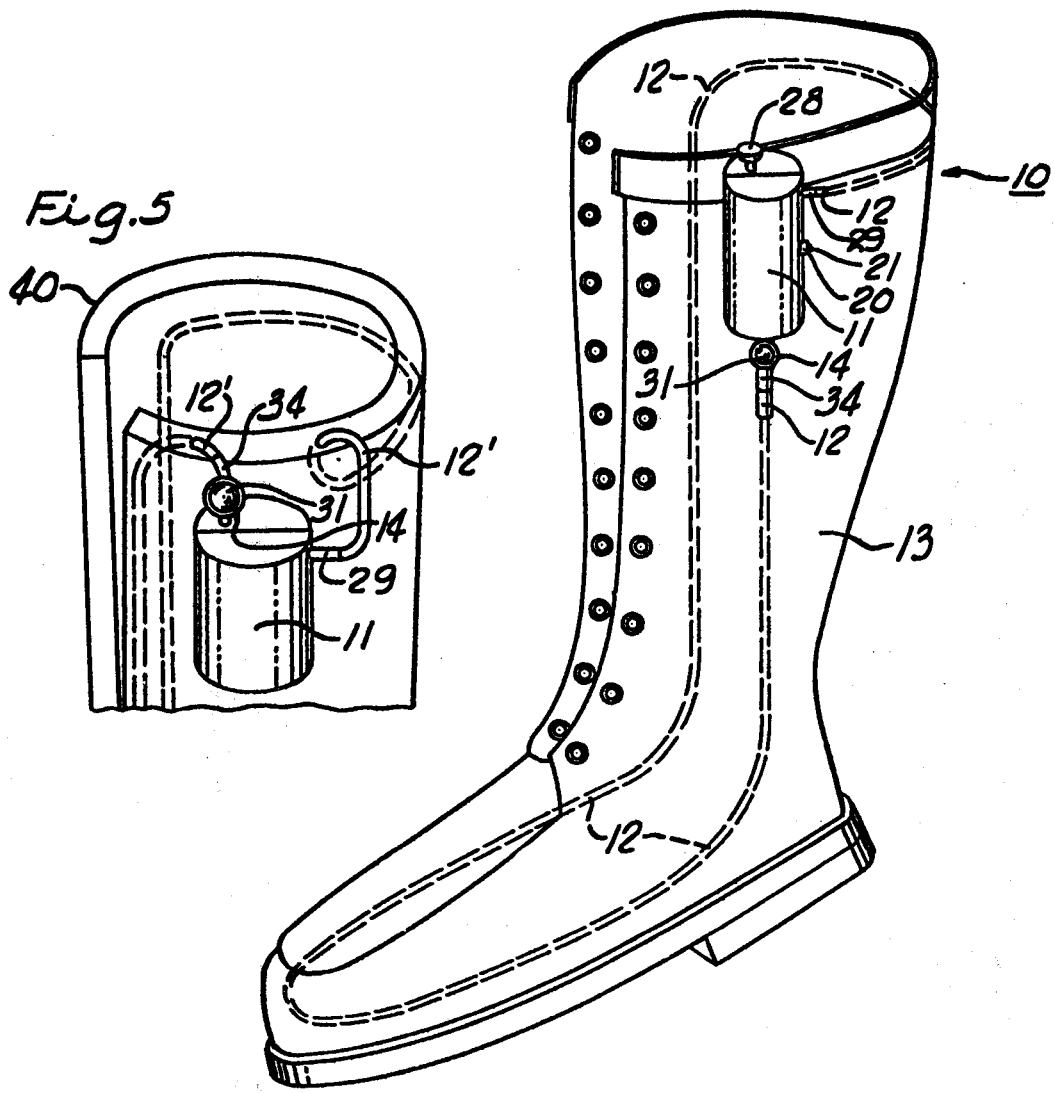

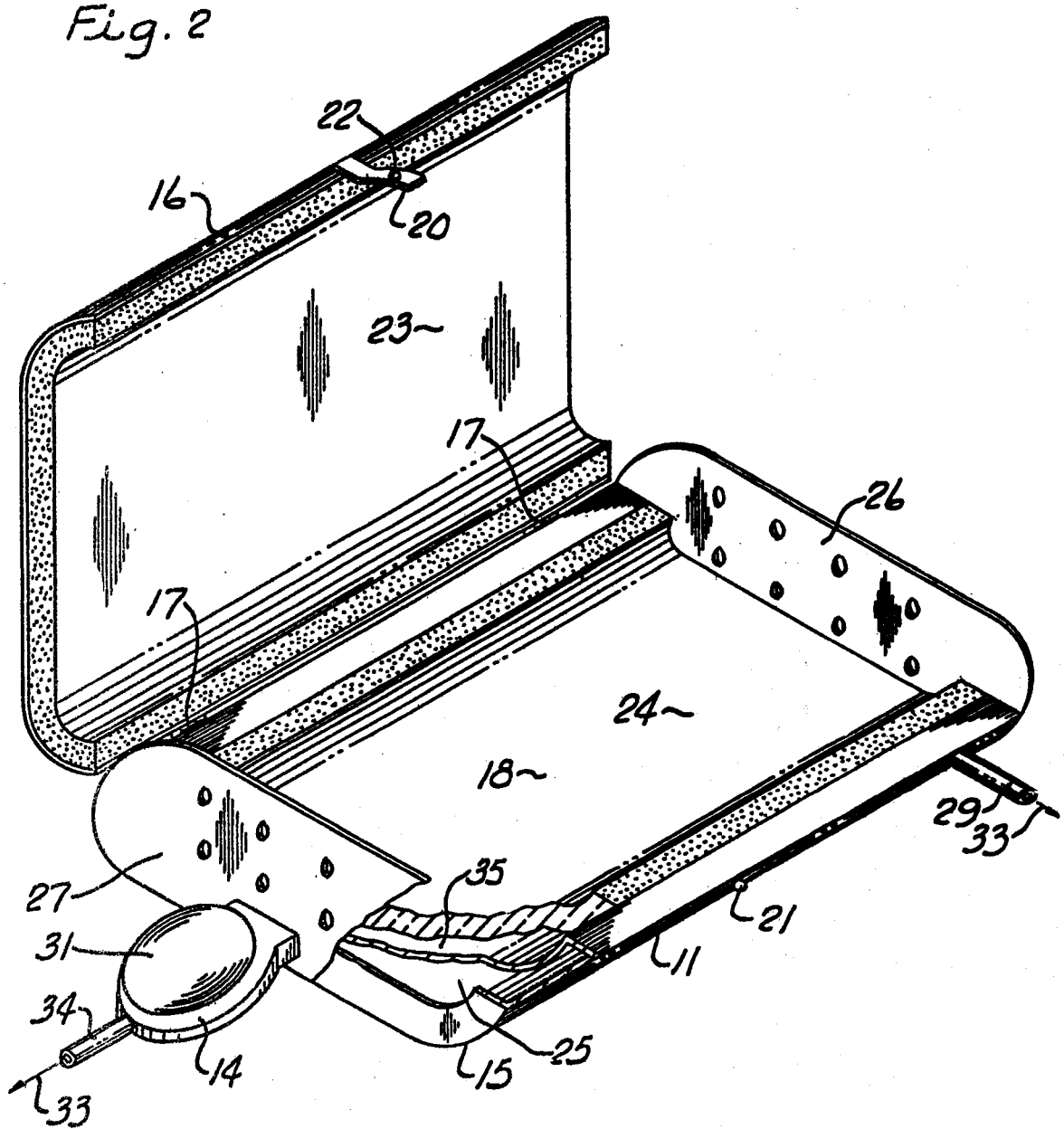

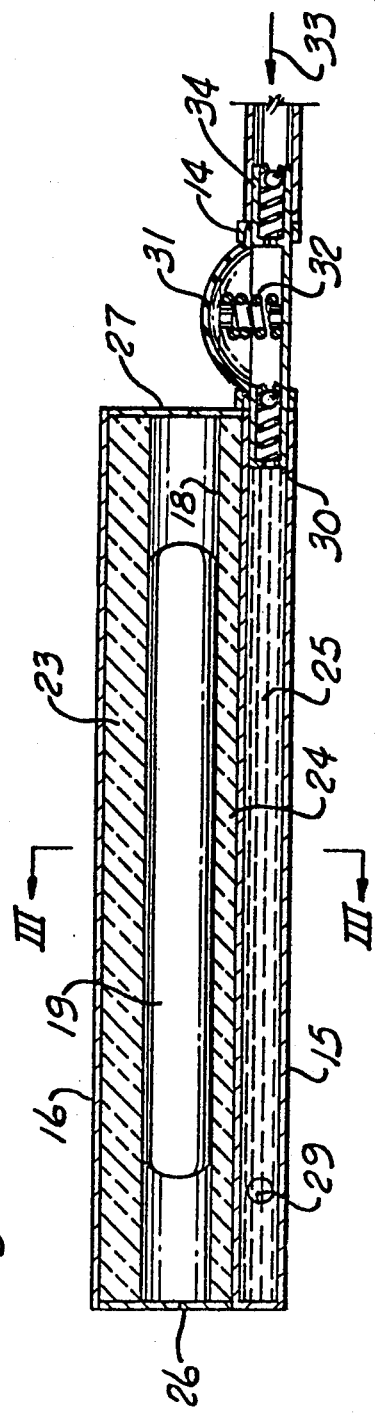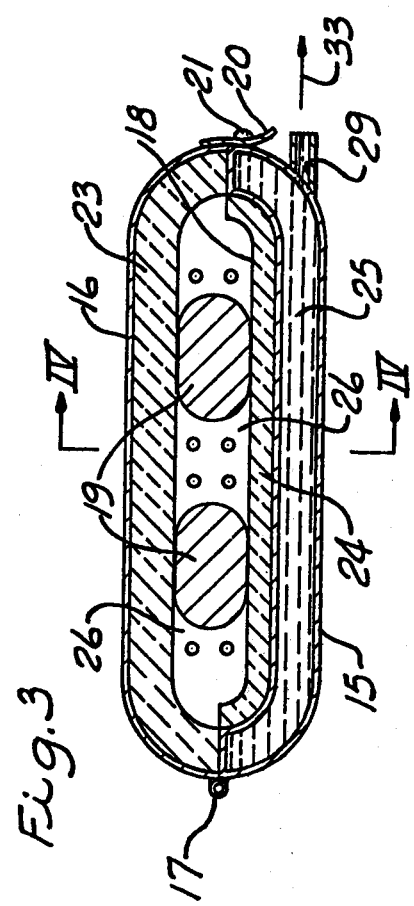

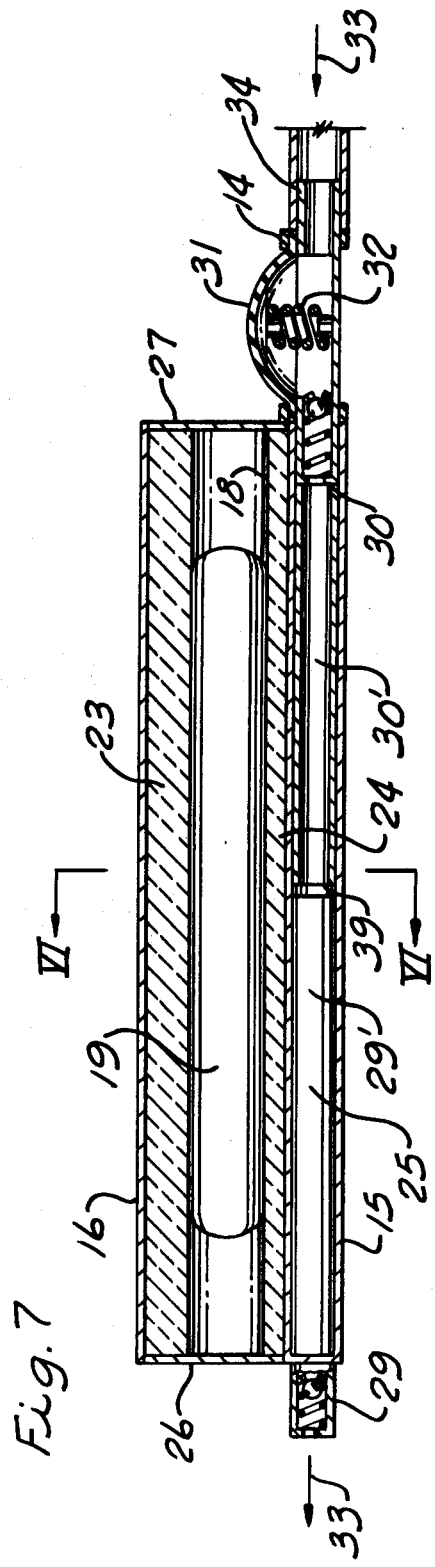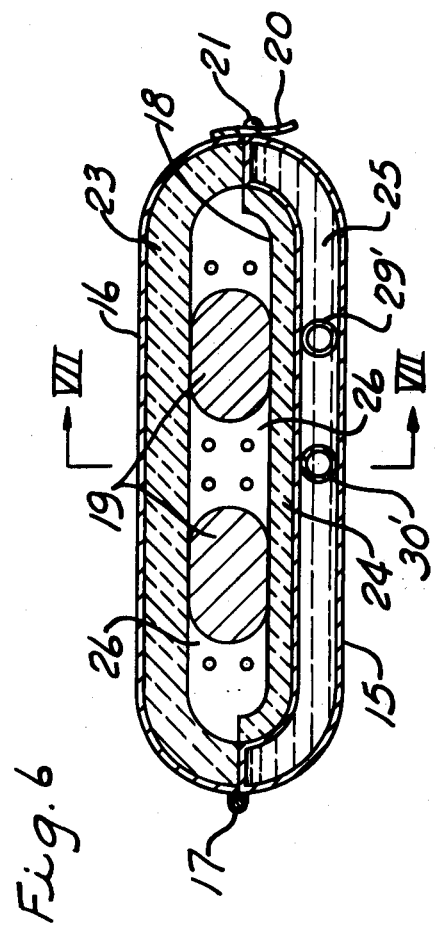

Fig. 8
Fig. 9
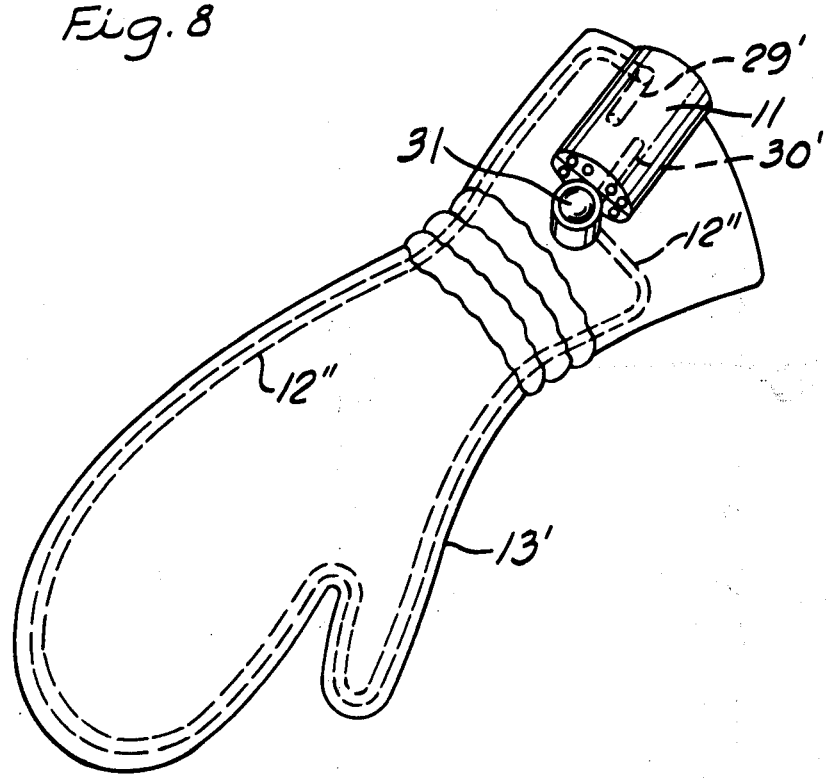
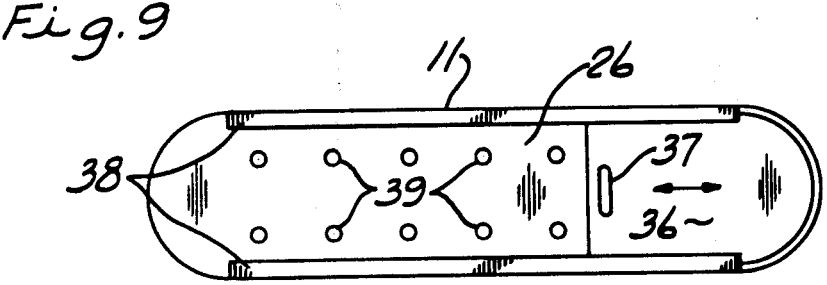

PORTABLE FURNACE FOR WEARING APPAREL

CROSS REFERENCE TO RELATED APPLICATION

This application is a continuation-in-part of U.S. Application Ser. No. 875,815 filed Feb. 7, 1978.

BACKGROUND OF THE INVENTION

The present invention relates to portable furnaces and more particularly to compact furnaces or warmers to be carried on the person for circulating heat in wearing apparel such as gloves or boots.

Boot warmers wherein a hot liquid is circulated within a boot have been known in the past, for example, as illustrated in U.S. Pat. No. 518,579 issued to Annenberg et al and in U.S. Pat. No. 1,199,914 issued to Mossor. However, such boot warmers provide no compact means for heating the fluid and further require a rather awkward operation in getting the heated fluid into the boot cavities.

U.S. Pat. No. 912,527 issued to Batter on Feb. 16, 1909 discloses a portable foot and body warmer wherein a heater unit of relatively large size is attached to the individual's belt and fluid conduit tubes pass from the individual's belt down his legs and into his shoes or boots. Hand manipulated pumps are provided at the knee level to pump or circulate the fluid throughout the conduits. However, such an apparatus is extremely cumbersome and it is also relatively impractical in this day and age, and it is rather obvious that hunters and outdoor workers would not tolerate such a large amount of paraphernalia and tubes running down the legs and about the waist.

Liquid heater units for body warming purposes which are much more compact than that illustrated in Batter Pat. No. 912,527 have been developed as may be seen in U.S. Pat. No. 3,737,620. However, this compact heater unit while being light weight and apparently very effective, is relatively complex and requires the use of nuclear fusion. The expense of such a device would clearly be beyond the reach of the average hunter or outdoor worker. In addition, this reference and the aforementioned references do not teach how any of the devices disclosed could be more conveniently and economically and compactly utilized as a boot or glove warmer.

A major disadvantage of the economical heating units of the prior art which are utilized to circulate a heated liquid through wearing apparel is that these heating units must be used substantially in an upright position and will not effectively operate at any or all attitudes. In addition, the liquid furnaces of the prior art are, by necessity, too large in size and are cumbersome.

A principle object of the present invention is to eliminate these disadvantages of the prior art and to provide a compact heating system for wearing apparel which is much more convenient and less expensive than the devices of the prior art.

SUMMARY OF THE INVENTION

The portable furnace of the present invention for generating and circulating heat in wearing apparel such as gloves or boots or the like comprises a compact insulated case which is capable of being carried on a person, and which is provided with a cavity therein which is adapted to be open to receive slow burning solid fuel agglomerates in the cavity for combustion. A liquid reservoir is also provided in the case and positioned for radiant heat transfer from ignited fuel agglomerates retained within the aforementioned cavity to heat the liquid contained within the reservoir. A flexible liquid conduit having both ends thereof connected for circulation of heated liquid from the reservoir through the conduit in a closed circuit is provided for circulation of heated liquid from the reservoir through the conduit. A pump is provided for hand manipulation in order to circulate the heated liquid from the reservoir through the conduit only on demand.

The conduit may be adapted for circulation of heated liquid from the reservoir within a piece of wearing apparel such as a glove or boot, and the compact furnace with its pump is readily attached to the wearing apparel itself, such as to the cuff of a glove or the top of a boot.

The portable furnace of the present invention has the advantage that the entire unit is connected to and part of the glove, boot or boot liner itself, and there are no awkward fluid lines to be run up the pant legs or arms of the wearer or other units to attach to other portions of the body. Everything is within one compact unit on the glove, boot or boot liner itself.

The pump utilized with the furnace of the present invention preferably consists of a hand operable diaphragm pump with check valves for unidirectional liquid flow in the flexible conduit.

In addition, it is also preferable that the furnace unit include conduit extensions which extend the opposite ends of the aforementioned flexible conduit into the midinterior of the reservoir. Thus, this permits the pump to circulate liquid from the reservoir into the conduit no matter in what attitude the furnace is positioned. In other words, no matter whether the furnace unit is upside down or rightside up, the ends of the conduit will always be in contact with liquid within the reservoir of the furnace unit.

The heat of the liquid within the reservoir may be readily regulated by the number of fuel agglomerates which are inserted into the furnace case or cavity, and ignited. The temperature of the liquid may also be regulated by the type and thickness of the insulation positioned between the solid fuel agglomerates and the liquid reservoir. The heat may also be further regulated by the type of solid fuel agglomerate utilized. Some may be provided which burn hotter than others. These fuel agglomerates generally contain an assistant combustion agent which produces oxygen with combustion.

The fuel agglomerate cavity within the furnace unit may generally be described as having top and bottom walls and side walls, with one side wall providing a heat exchanger for the radiant heat transfer from the fuel cavity to the reservoir containing the liquid. These side walls, except the aforementioned one side wall which provides the heat exchanger, are insulated for the prevention of heat loss or transfer. The one remaining heat exchanger side wall is only lightly insulated on the inside of the cavity so as to permit heat transfer through this heat exchanger wall from the fuel cavity to the liquid reservoir, but at the same time, the insulation prevents excessive moisture build up on this side wall which might otherwise be capable of extinguishing the solid fuel agglomerates which are under combustion in the cavity. Vent apertures are provided in at least the top wall, and generally in the top and bottom walls, to vent the combustion gases out of the furnace unit or cavity. A damper is also preferably provided to adjustably cover selected of these vent apertures to thereby provide additional control over the combustion of the fuel agglomerates and the resultant temperature at which the liquid contained within the reservoir is maintained.

BRIEF DESCRIPTION OF THE DRAWINGS

Other objects and advantages appear in the following description and claims.

The accompanying drawings show, for the purpose of exemplification without limiting the invention or the claims thereto, certain practical embodiments illustrating the principles of this invention wherein:

FIG. 1 is an isometric view in side elevation of the portable furnace of the present invention as utilized in a conventional boot.

FIG. 2 is an enlarged isometric view of the heater and pump unit of the present invention with the cover of the heater case opened to expose the cavity for receiving the fuel agglomerates and with other portions removed to expose the interior of the liquid reservoir.

FIG. 3 is a view in mid-cross section of the heater unit illustrated in FIG. 2 and as seen along line III—III with the cover closed and the solid fuel elements inserted, or as seen along section line III—III of FIG. 4.

FIG. 4 is a sectional view of the heater unit illustrated in FIG. 3 as seen along section line IV—IV illustrating the interiors of the heater unit and the pump.

FIG. 5 is an isometric view of a felt boot liner in section with the heat exchanger or heater unit and pump assembly of the present invention installed to the top thereof.

FIG. 6 is a view in mid-cross section of the heater unit illustrated in FIG. 2 with modifications and as seen along section line III—III with the cover closed and the solid fuel elements inserted, or as seen along section line VI—VI of FIG. 7.

FIG. 7 is a sectional view of the heater unit illustrated in FIG. 6 as seen along section line VII—VII illustrating the interiors of the heater unit and the pump.

FIG. 8 is an isometric view in side elevation of the portable furnace of the present invention as utilized in conjunction with a conventional glove.

FIG. 9 is an end view of the heater unit illustrated in FIG. 4 showing the details of a damper control.

DETAILED DESCRIPTION OF THE DRAWINGS

Referring to FIG. 1, the wearing apparel furnace or warmer and boot combination 10 of the present invention includes a portable compact heater unit or heat exchanger 11 having a liquid conduit 12 circulating throughout and within boot 13 in order to circulate heated liquid from the heat exchanger unit 11. Heater liquid is pumped from unit 11 through conduit 12 by means of hand manipulated pump 14.

Referring particularly to FIGS. 2, 3 and 4, heater unit 11 is relatively compact and includes a compact case 15 having a cover 16 which is hinged at 17 to the remainder of case 15 and opens as indicated in FIG. 2 to provide cavity 18 therein to receive slow burning solid fuel agglomerates 19 therein for burning. Fuel agglomerates 19 are conventional fuel agglomerates which may be purchased on the open market. One such fuel agglomerate is sold under the name of World Famous Sales Company Solid Fuel Sticks. These fuel sticks are commonly used in hand warmers. Another useable fuel is described in U.S. Pat. No. 3,547,100.

Cover 16 is secured in its closed position as best illustrated in FIG. 3 by means of spring clip 20 which rides over and receives projection 21 within slot 22.

Cavity 18 is insulated by means of insulation 23 in cover 16 and insulation 24 in the bottom of cavity 18. This insulation may be any conventional insulation such as fiberglass matting, and insulation sheet 23 is slightly thicker than insulation sheet 24. Insulation sheet 23 prevents undue loss of heat to the exterior. Center insulation sheet 24 in the bottom of cavity 18 is utilized to prevent solid fuel stick 19 from overheating or superheating the liquid contained in reservoir 25. If the fuel sticks 19 were permitted to directly contact the metal back wall 35, which is the heat exchange wall for the liquid reservoir 25, hot spots could be readily generated and the liquid contained therein could be overheated. Insulation 24 also prevents condensation build-up on wall 35 which could otherwise extinguish the burning fuel agglomerates. It is generally desirable to maintain the heat of the liquid in reservoir 25 to be about 130° F.

Case 15 is provided with a perforated top 26 and a perforated bottom 27 which are welded to the main body of the case. The perforations in top and bottom walls 26 and 27 provide adequate ventilation and oxygen supply for the slow burning solid fuel agglomerates 19.

The entire case 15, with the exception of insulation 23 and 24 contained therein, is manufactured of a suitable metal such as chrome plated steel. As is best illustrated in FIG. 1, a filler spout 28 is provided at the top of the case 15 and provides access to liquid reservoir 25 for initially filling the reservoir with a suitable heat transfer liquid such as antifreeze, or a combination of water and antifreeze. Filler opening 28 is provided with a suitable plug.

Reservoir 25 is provided with an outlet 29 and an inlet 30. Hand pump 14 is secured to the bottom of case 15 by means of the outlet tube 30 which penetrates into reservoir 25. Hand pump 14 is a conventional double check valve pump having a flexible diaphragm 31 which is pumped or depressed by one's finger against the resistance of return coil spring 32 to pump liquid through pump 14 as indicated by arrows 33.

The inlet of pump 14 is indicated at 34 and conduit 12 is connected at one end to inlet 34 with a force fit and at the other end with a force fit over hot liquid discharge or outlet 29.

The entire heater unit 11 together with pump 14 which is secured thereto, are attached to the boot top as indicated in FIG. 4 by any conventional means such as a pocket or an adhesive. In FIG. 1, the entire unit is attached with an adhesive and the connection of conduit 12 to the unit also assists in holding it in position.

In order to operate the portable furnace of the present invention, antifreeze or other suitable liquids are poured into the system of reservoir 25 and conduit 12 by means of filler opening 28. While doing this, pump 14 is manipulated to fully circulate the liquid being poured into the system throughout the conduit and to purge air from the system back out through filler inlet 28. Once the system is filled, one or two fuel sticks 19 are ignited at one end thereof by a match and the ignited fuel sticks are laid in cavity 18 as illustrated in FIGS. 3 and 4 and cover 16 is snapped shut and the boots are ready to wear in cold weather.

The wearer can manipulate pump 14 every 15 minutes to half hour, or as desired, to circulate heated liquid in reservoir 25 through conduit 12 thereby warming the interior of boot 13.

The entire unit and combination boot and heater unit are very compact and the portable furnace of the present invention does not interfere with the normal activity of the boot wearer and requires no tubes or anything else attached elsewhere on the person of the wearer.

As illustrated in FIG. 5, the portable furnace of the present invention may be provided in combination with a boot liner 40 with conduit 12' circulating throughout the boot liner 40. Felt boot liner 40 is of the conventional type which is inserted within a water impervious boot casing such as indicated at 13 in FIG. 1. Thus, the felt liner and portable furnace combination may be sold as a separate unit and inserted into a wearer's existing boot casing.

The conduit 12' exits from the top of felt boot liner 40 so that the boot liner may be conveniently inserted within a boot casing and then the heater unit 11 hangs over top of the outside boot casing and may be secured thereto by a pocket on the outside of the boot casing or any other conventional securing means such as an adhesive or an expansion strap or belt strap.

In either situation, the heater unit 11 is exposed for proper ventilation and pump 14 is also exposed for easy access and manipulation as required.

In order to fill the system illustrated in FIG. 5 with the heat transfer liquid, one need only remove conduit 12' from either outlet 29 or inlet 34 and fill the device through the opening or a separate filler opening may be provided as is the case with the unit illustrated in FIG. 1.

Referring to FIGS. 6 and 7, basically the heating unit or furnace here illustrated is identical to that illustrated in FIGS. 3 and 4, and accordingly the same reference numerals designate the same elements. In this embodiment, the outlet 29 is positioned at the top 26 of the reservoir 25. Inlet 30 and outlet 29 are both respectively provided with extension conduits 30' and 29', which extend into reservoir 25 to the midsection thereof at position 39.

The reason for extensions 30' and 29' is that they effectively extend the ends of conduit 12 into the center of the reservoir so that no matter what position or attitude the furnace or heater unit is positioned, the liquid within reservoir 25 will always be in contact with the centrally located open ends of conduit extensions 30' and 29' so that water may be circulated by pump 31 even though the entire heater unit may be positioned upside down, horizontally, sideways, etc. In this Figure also, instead of positioning the two check valves immediately on either side of pump 31, one of the check valves is positioned at inlet 30 and the other is positioned at outlet 29. This assures that the heated liquid in reservoir 25 will not accidentally circulate into the flexible conduit 12 by convection.

Turning next to FIG. 8, here the same heater unit or portable furnace 11 is illustrated in combination with a glove 13' and this combination operates in the identical manner as the description given in connection with a boot as illustrated in FIG. 1. Here the heater unit 11 is secured to the stiff cuff portion of the glove 13' and the flexible conduit 12" circulates throughout the glove for circulation of liquid on demand by manipulation of pump 31. Also, this Figure in dashed outline further illustrates the conduit extensions 30' and 29' which extend into the mid interior of the liquid reservoir.

FIG. 9 is a top end view of the portable furnace 11 illustrating the top end 26 with its numerous vent apertures 39. In this Figure, a damper 36 is illustrated which is slidably received at its edges in slide guides 38. Damper 36 may be slid to the left or right as illustrated by the arrow by manipulation of the handle 37 secured thereto. Thus, damper 36 may be slid to the left to cover more of the apertures 39 and thus act as a damper control to further control the burning capabilities of the agglomerates 19 contained within the case. This damper thus provides an additional temperature control and also provides a control for the rate of burning of the solid fuel agglomerates.

We claim:

1. A portable furnace for generating and circulating heat in wearing apparel or the like comprising a compact insulated case capable of being carried on a person and having a cavity therein and further adapted to be opened to receive slow burning solid fuel agglomerates in said cavity for combustion, a liquid reservoir in said case positioned for radiant heat transfer from ignited fuel agglomerates in said cavity to a liquid in said reservoir, a flexible liquid conduit having both ends thereof connected for circulation of the heated liquid from said reservoir through said conduit in a closed circuit adapted for circulation of heated liquid from said reservoir through said conduit, and pump means connected to said conduit for hand manipulation thereof to circulate heated liquid from said reservoir through said conduit on demand, said cavity having top and bottom walls and side walls with one side wall providing a heat exchanger for said radiant heat transfer, said side walls except said one side wall being insulated for prevention of heat transfer, said one heat exchanger side wall being lightly insulated on the inside such as to permit heat transfer through said one side wall from said cavity to said reservoir but at the same time prevent excessive moisture buildup on said one side wall which would otherwise be capable of extinguishing a solid fuel agglomerate under combustion in said cavity, and vent apertures in at least one of said top and bottom walls.

2. The portable furnace of claim 1 including damper means adapted to adjustably cover selected of said vent apertures.

3. The portable furnace of claim 1 wherein said vent apertures exit in both said bottom and top walls.

4. The portable furnace of claim 1 including a glove, said flexible conduit adapted for circulation of heater liquid from said reservoir within said glove.

5. The portable furnace of claim 1 wherein said pump means consists of a hand operable diaphragm pump with check valves for unidirectional liquid flow in said conduit.

6. The portable furnace of claim 1 including conduit extensions which extend the opposite ends of said conduit into the mid interior of the reservoir.

7. The portable furnace of claim 6 wherein said conduit extensions extend into said reservoir from opposite directions.

8. The portable furnace of claim 1 including at least one slow burning solid fuel agglomerate received in said cavity for combustion.

9. The portable furnace of claim 8 wherein said agglomerate contains an assistant combustion agent producing oxygen with combustion.

10. The portable furnace of claim 1 adapted to receive a plurality of slow burning solid fuel agglomerates in said cavity.

* * * * *